(12) United States Patent
Eisenmann et al.

(10) Patent No.: US 7,240,565 B2
(45) Date of Patent: Jul. 10, 2007

(54) STRIP EJECTOR

(75) Inventors: Martin Eisenmann, Ottobrunn (DE); Otto Rzehak, München (DE); Ralph Pinzenöller, München (DE); Johann Stapfner, Kolbermoor (DE); Norbert Pöllmann, Eching (DE)

(73) Assignee: LRE Medical GmbH, Munich (DE)

( * ) Notice: Subject to any disclaimer, the term of this patent is extended or adjusted under 35 U.S.C. 154(b) by 132 days.

(21) Appl. No.: 11/122,347

(22) Filed: May 5, 2005

(65) Prior Publication Data
US 2005/0256382 A1 Nov. 17, 2005

(30) Foreign Application Priority Data
May 7, 2004 (DE) .................. 10 2004 022 757

(51) Int. Cl.
*G01N 3/02* (2006.01)
(52) U.S. Cl. ........................................ 73/859
(58) Field of Classification Search ................ 73/853, 73/856, 859; 435/4; 604/59, 60, 61; 609/59; 422/68.1
See application file for complete search history.

(56) References Cited
U.S. PATENT DOCUMENTS

| 4,780,283 | A * | 10/1988 | Meinecke et al. ........ 422/82.05 |
| 5,281,395 | A * | 1/1994 | Markart et al. .......... 422/82.05 |
| 5,424,035 | A * | 6/1995 | Hones et al. ................ 422/55 |
| 5,872,713 | A * | 2/1999 | Douglas et al. ............... 702/85 |
| 6,827,899 | B2 * | 12/2004 | Maisey et al. ................ 422/61 |
| 6,908,008 | B2 * | 6/2005 | Pugh .......................... 221/135 |
| 2002/0114735 | A1 * | 8/2002 | Markart ..................... 422/68.1 |
| 2004/0156037 | A1 * | 8/2004 | Mawhirt et al. .............. 356/39 |
| 2005/0061700 | A1 * | 3/2005 | Windus-Smith et al. .... 206/438 |
| 2005/0163657 | A1 * | 7/2005 | Childers et al. ............. 422/50 |
| 2006/0133956 | A1 * | 6/2006 | Hamanaka ................. 422/68.1 |
| 2006/0189895 | A1 * | 8/2006 | Neel et al. .................. 600/584 |

* cited by examiner

*Primary Examiner*—Edward Lefkowitz
*Assistant Examiner*—Freddie Kirkland, III
(74) *Attorney, Agent, or Firm*—McCormick, Paulding & Huber LLP

(57) ABSTRACT

A strip ejector removes a longitudinal test strip (12), which has at least one test field for wetting by a fluid, from a measuring device that optically or amperemetrically measures such test strip. The ejector includes a clamping jaw holder (14), and at least two clamping jaws (18) arranged on the clamping jaw holder at a distance from one another. The jaws are moveable relative to one another between a freeing position in which the spacing between their clamping surfaces is larger than the width of a test strip (12), and a clamping position in which their clamping faces respectively engage parallel edges (22) of the test strip (12). An actuating element (24) moveably supported on the clamping jaw holder (14) has at least one control surface 30 arranged at an angle to the movement direction of the actuating element. The control surface cooperates with a countersurface (32) formed on a least one of the clamping jaws (18) to move the clamping jaw (18) from its freeing position to its clamping position upon a movement of the actuating element (24).

13 Claims, 4 Drawing Sheets

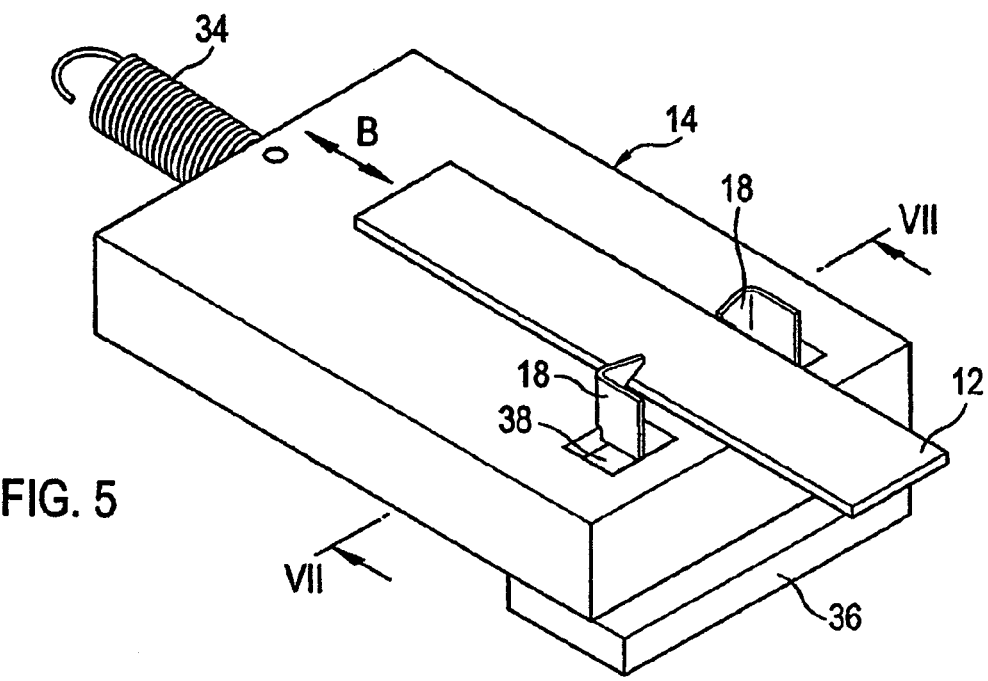
FIG. 5
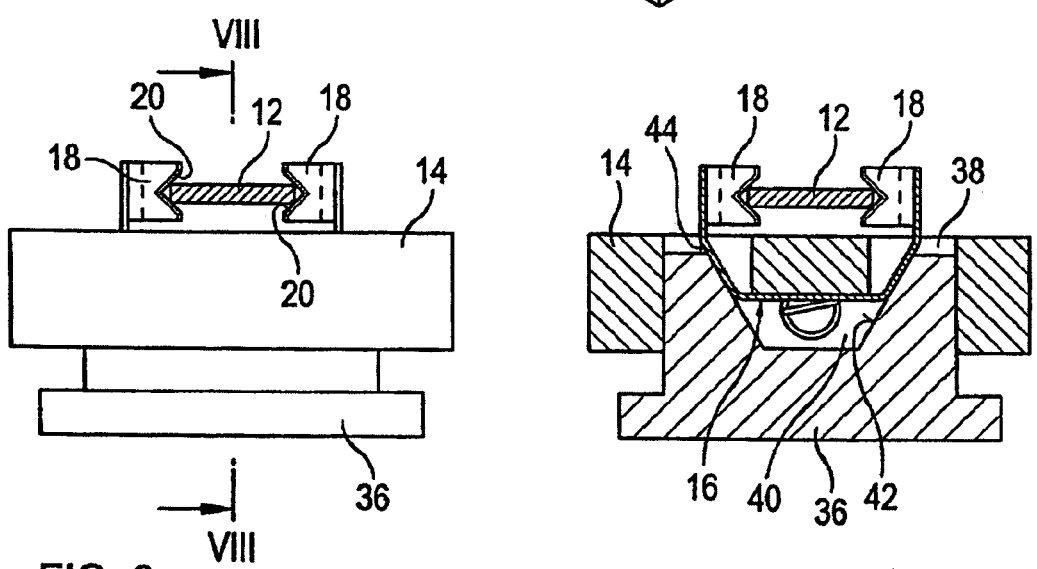
FIG. 6
FIG. 7
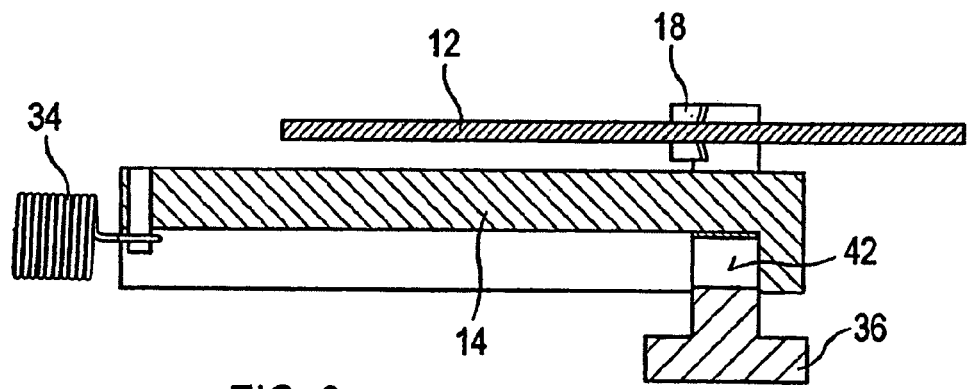
FIG. 8

STRIP EJECTOR

CROSS REFERENCE TO RELATED APPLICATIONS

The priority of German Patent Application 10 2004 022 757.8 of May 7, 2004 is claimed, and the disclosure of the German Patent Application is incorporated by reference.

FIELD OF THE INVENTION

The invention concerns a strip ejector for removing an elongated test strip, which has at least one test field to be wetted by a fluid, from a measuring device for optically or amperemetrically measuring such test strips.

BACKGROUND OF THE INVENTION

Measuring devices of the previously mentioned kind are used for example by diabetics to monitor their blood sugar levels. However, these measuring devices are also used to analyze other body fluids. The test strips are in the meantime, relatively small to on one hand save on the use of expensive test strip material and also on the other hand to make possible a measurement with a relatively small amount of the fluid to be tested. The small size of the test strips makes their handling more difficult. Especially, it is hard to remove the test strips from the device without coming into contact with the fluid applied to the test strips.

The invention has as its object, the provision of a strip ejector making possible by simple means the easy removal of a test strip from the measuring device.

SUMMARY OF THE INVENTION

For the solution of this object a test strip ejector of the previously mentioned kind according to the invention includes a clamping jaw holder, at least two clamping jaws, arranged on the clamping jaw holder at a spacing from one another. The jaws are movable relative to one another between a freeing position in which the opposed spacing of their clamping surfaces is larger than the width of a test strip and a clamping position in which their clamping surfaces engage parallel edges of the test strip. An actuating element is moveably supported on the clamping jaw holder and has at least one control surface angled relative to the movement direction of the actuating element. The control surface cooperates with a countersurface formed on at least one clamping jaw to move the clamping jaw upon a movement of the actuating element from its freeing position to its clamping position.

By the effect of the actuating element and through the cooperation of the control surfaces and their associated countersurfaces on one another, the clamping jaws are moved and clamp the test strip between them. Then by shifting of the clamping jaw holder the test strip can be moved out of the strip receiving compartment of the measuring device without it having to be grasped once again.

Preferably the clamping jaws are biased to their freeing position, so that after the release of the actuating element they automatically return to their freeing position. Preferably the clamping jaws are formed on the longitudinal ends of a C-shaped bent clamping spring. By tensioning of the C-shaped clamping spring in its middle section the clamping jaws are moveable and at the same time are biased toward their freeing position.

To assure a secure gripping of the test strip, in a preferred embodiment, the end sections of the clamping spring which are turned toward one another have V-shaped notches for receiving the edges of the strip.

In a simply constructed embodiment the actuating element has a recess on its end facing the clamping spring which recess widens in going toward the end of the actuating element, with the side surfaces defining the recess forming the control surfaces.

The invention further concerns a measuring device for optically or amperemetrically measuring test strips each of which test strips has at least one test field to be wetted by a fluid. The device includes a housing with a strip receiving compartment and a service field, a measuring arrangement, evaluation and control device, and a current source. One such measuring device, known in itself, according to the invention has a strip ejector of the previously mentioned kind which is arranged in the measuring device with the clamping jaws lying respectively on both sides of the strip receiving compartment. The clamp is a jaw holder movable on the housing parallel to the insertion direction of the test strips between a rest position and an ejecting position. Advantageously, the clamping jaw holder is biased toward its rest position so that it automatically returns to this position.

The clamping jaw holder can be fastened to a housing wall, with the sliding movement being provided for by way of a groove/rail guide. For simple assembly the arrangement can be such that the clamping jaw holder is snapped on the housing wall. Since both the housing and the clamping jaw holder can be made of plastic, the elasticity of the plastic material generally is sufficient to permit a snapping effect.

In a preferred embodiment, the housing wall which carries the strip ejector is the battery cover for a battery compartment formed in the housing. This part can not only be easily made with the elements necessary for the attachment of the strip ejector, but it also makes possible a convenient mounting of the strip ejector.

In one embodiment the actuating element is formed as a pusher which is supported on the clamping jaw holder for slidable movement parallel to the movement direction of the clamping jaw holder. In this way the transfer of the clamping jaws to their clamping position and the movement of the clamping jaw holder to its ejecting position takes place in a single movement. Alternatively hereto the actuating element can be made as a push button which is supported on the clamping jaw holder for movement perpendicularly to the movement direction of the clamping jaw holder.

BRIEF DESCRIPTION OF THE DRAWINGS

The following description in combination with the accompanying figures explains the invention by way of an exemplary embodiment.

FIG. 5 is a perspective view of a second form of the strip ejector of the invention.

FIG. 6 is a front view corresponding to that of FIG. 3 of the strip ejector according to FIG. 5.

FIG. 7 is a view through the strip ejector taken along the lines VII—VII in FIG. 5.

FIG. 8 is a view through the strip ejector taken along the lines VIII—VIII in FIG. 6.

DESCRIPTION OF THE PREFERRED EMBODIMENTS

Figure 1:
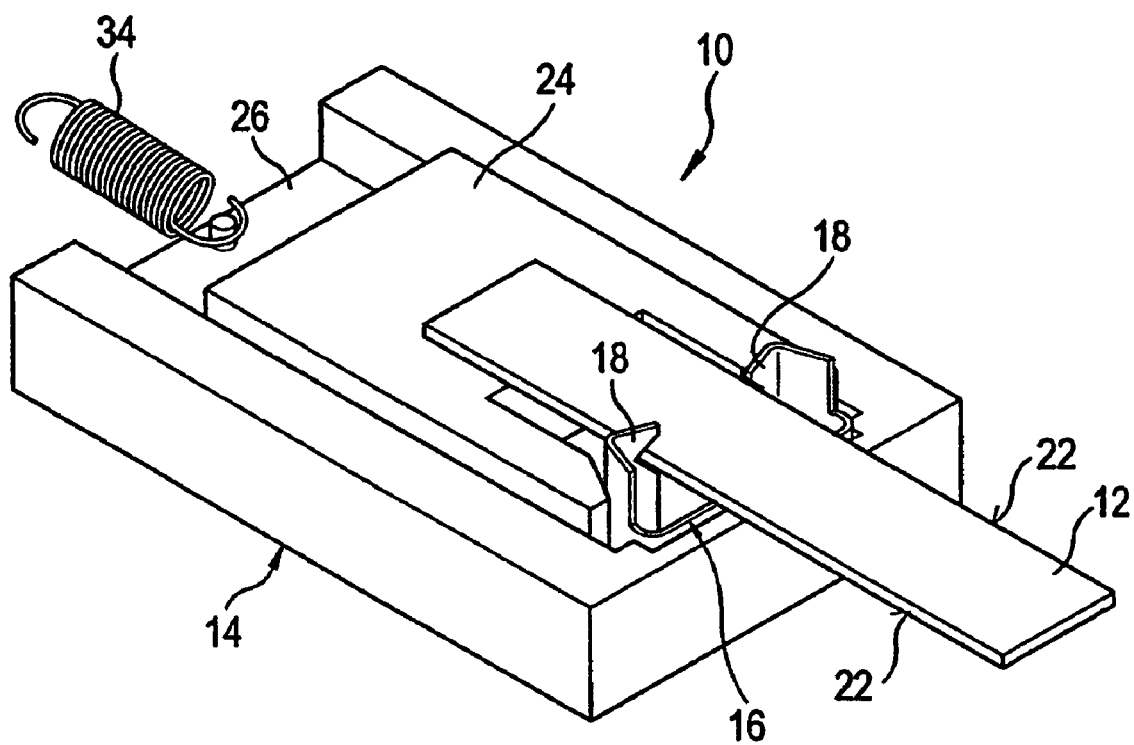
FIG. 1 is a perspective view of a first embodiment of the strip ejector of the invention.

FIG. 1 shows a strip ejector, indicated generally by the reference numeral 10, which ejector serves to grasp test strip 12 and to push or pull it out of a measuring device so that the strip can be thrown directly to a waste site without the user having to touch it. The strip ejector includes a plate-shaped clamping jaw holder 14 in which a clamping spring 16 is held. The clamping spring 16 is a strip-shaped leaf spring whose ends are bent inwardly and form resilient clamping jaws 18. The clamping jaws have a spacing from one another which is somewhat larger than the width of the test strip 12. Further, on the edges facing one another, each clamping jaw has a V-shaped notch 20 in which a longitudinal edge 22 of the test strip 12 is captured when the clamping jaws 18 are moved toward one another to clamp the test strip 12 between the jaws.

Figure 2:
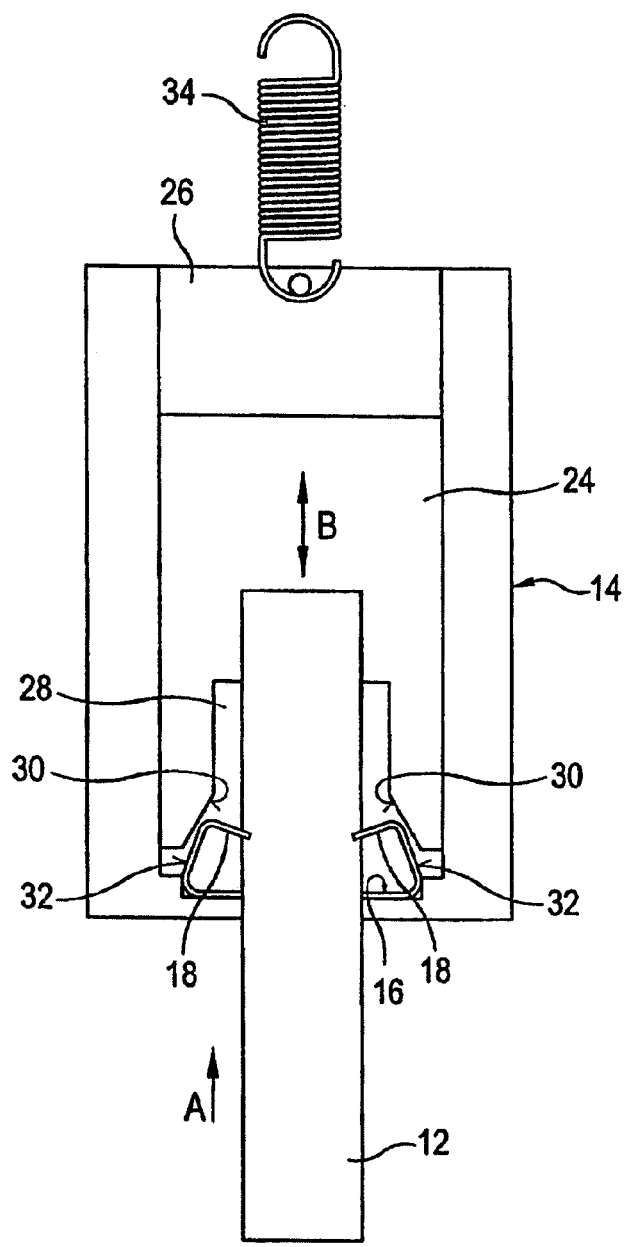
FIG. 2 is a plan view of the strip ejector of FIG. 1.
Figure 3:
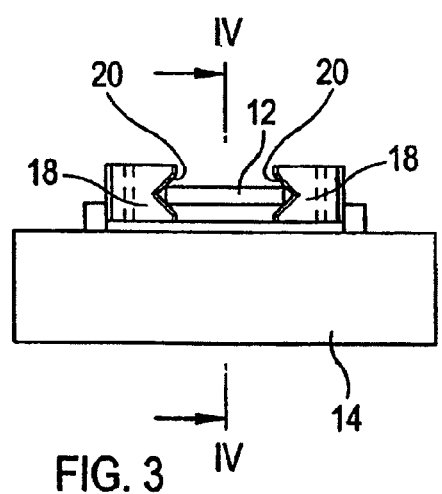
FIG. 3 is a front view of the strip ejector taken in the direction of the arrow A of FIG. 2.
Figure 4:
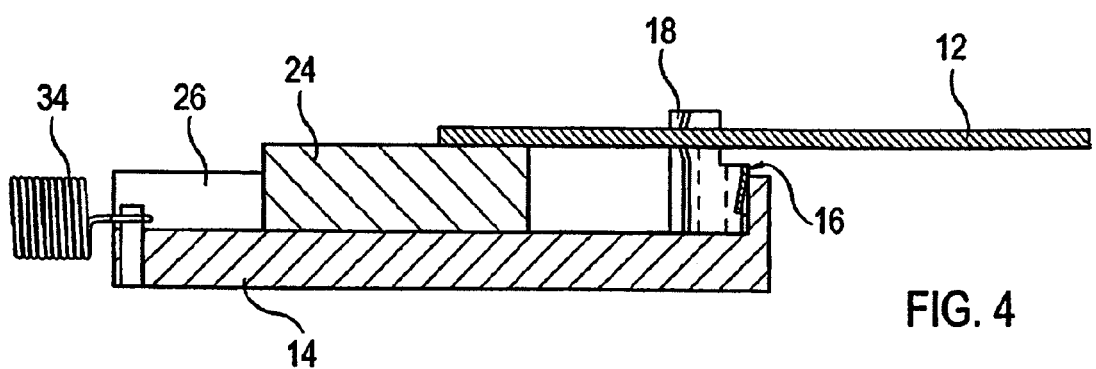
FIG. 4 is a view through the strip ejector taken along the line IV—IV in FIG. 3.

A pusher 24 which is slidable in a recess 26 of the clamping jaw carrier 14 in the direction of the double arrow B in FIG. 2 serves to control the clamping jaws 18. The pusher 24 has a recess 28 on the side facing the C-shaped bent clamping spring 16, and the recess 28 has lateral boundary surfaces which in going toward the end of the pusher 24 angled outwardly from one another. The so-formed angled surfaces constitute control surfaces 30 which upon a sliding of the pusher 24 in the direction toward the clamping spring 16 engage associated countersurfaces 32 on the outer sides of the clamping jaws 18 and press the clamping jaws 18 together so that the test strip 12 is grasped between the clamping jaws 18.

The clamping jaw holder 14 is arranged in a non-illustrated measuring device so that it is likewise movable in the direction of the arrow to an ejecting position, and is biased by a spring 34 to a rest position inside of the measuring device. Having pushed the clamping jaw holder 14 with the gripped test strip 12 into the ejection position, the user then releases the pusher 24, whereupon the clamping jaws 18, because of the biasing of the clamping spring 16, move clear of the test strip 12 so that the strip can fall to the waste site.

In the second form of the invention illustrated in FIGS. 5–8 the same parts are again indicated by the same reference numbers. The embodiment according to FIGS. 5–8 essentially differs from the first form in that instead of a pusher 24 a push button 36 is provided which is movable in a recess 38 of the plate-shaped clamping jaw holder 14 perpendicularly to the sliding direction B of the clamping jaw holder 14. The push button 36 has on its side facing the clamping spring 16 a recess 40 with angled side surfaces 42. The side surfaces constitute the control surfaces and are designed for engagement with countersurfaces 44 on the outer side of the clamping jaws 18. To grippingly receive the test strip 12 the push button 36 is pressed into the recess 38 so that the two clamping jaws of the C-shaped bent clamping spring 16 are moved toward one another and grasp the test strip 12. Then the plate-shaped clamping jaw holder 14 is pushed in the direction of the arrow B outwardly of the device into its ejection position. By releasing the push button 36, the test strip 12 is then freed so that it can fall to the waste site.

The inventive strip ejector can be designed so as to be included in a measuring device from the beginning, or it can be so formed as to be capable of being added to a measuring device at a later time.

Figure 9:
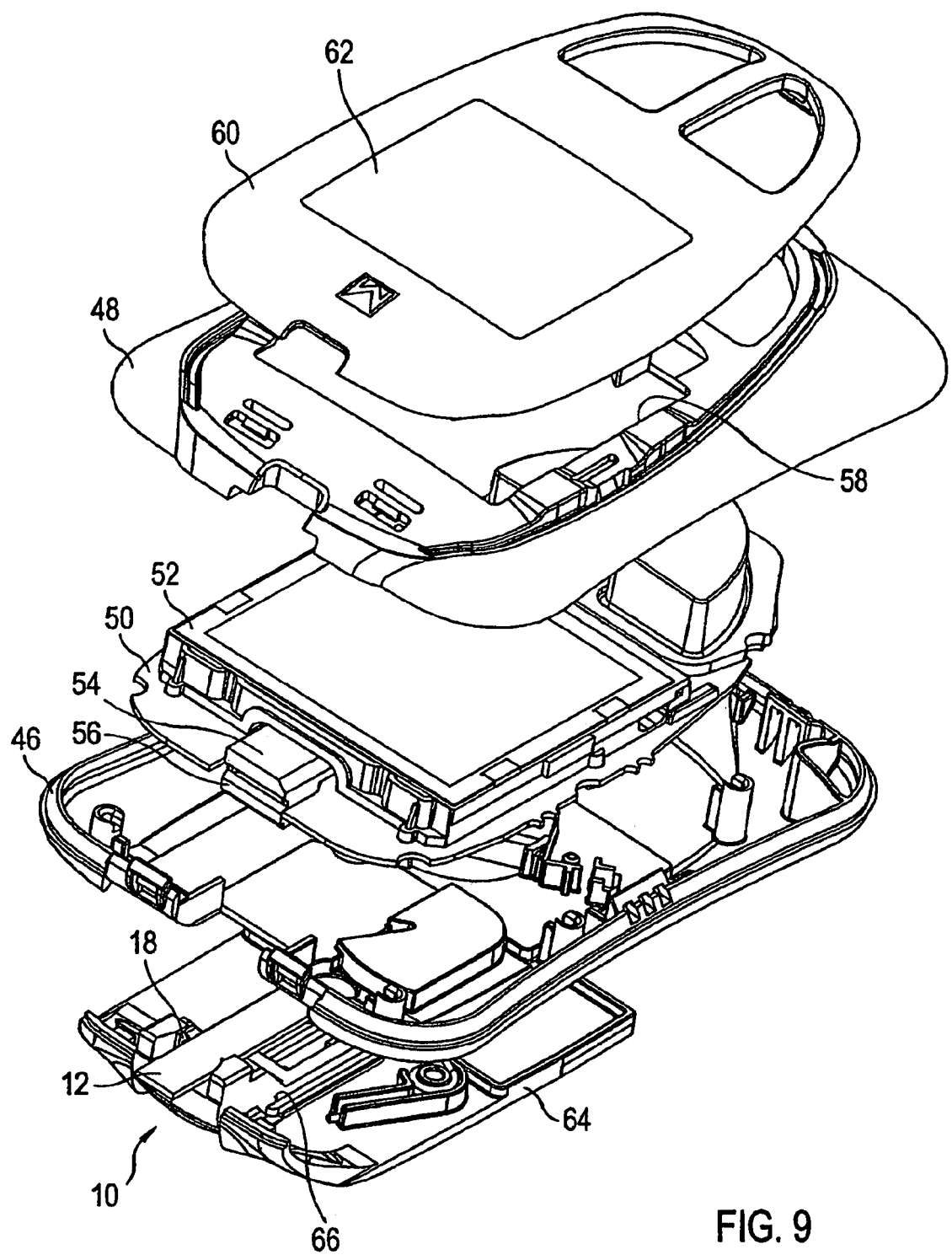
FIG. 9 is a fragmentary exploded illustration which shows the arrangement of the Strip Ejector in a measuring device.

FIG. 9 shows a fragmentary exploded illustration of a measuring device known in itself for the measurement of test strips, for example a device for monitoring blood sugar level. The device includes a housing bottom part 46 and a housing upper part 48 between which is enclosed an electronic circuitboard 50. The circuitboard carries the entire measuring system, that is for example, a measuring optical system, and a measuring and evaluation electronic system as well as an indicator field 52. Arranged on the electronic circuitboard 50 is further a strip port 54 with an input slot 56 for a test strip. The housing upper part has a frame opening 58 into which the indicator field 52 comes to lie when the housing bottom part 46 and the housing upper part are brought together to enclose the electronic circuitboard 50. The housing upper part 48 is then closed by an upper cover 60 with a window 62 for the indicator field 52.

On the under side of the housing bottom part 46 is a battery compartment not illustrated in detail, which compartment can be closed by a battery cover 64 having a recess 66 in which a strip ejector 10 is received. The arrangement is so designed that the clamping jaws 18 of the strip ejector 10 in the assembled device are positioned directly in front of the insertion slot 56 of the strip port 54. The test strip 12 illustrated in FIG. 9 in the case of the assembled device is naturally inserted into the strip port 54. The end extending out of the strip port 56 can be gripped by the clamping jaws 18 with the pusher 24 of the strip ejector 10 lying on the underside of the device cover 64 (not visible in FIG. 9). The parts 46 and 48 as well as their covers 62 and 64 are generally made of a plastic and can be snapped or screwed in assembly with one another.

The invention claimed is:

1. A strip ejector for the removal of an elongated test strip, which has at least one test field for wetting by a liquid, from a measuring device for optically or amperemetrically measuring such a test strip, comprising: a clamping jaw holder, at least two damping jaws arranged on the clamping jaw holder, each of the clamping jaws defining a damping surface, the clamping jaws being movable relative to one another between a freeing position in which the clamping surfaces are spaced apart a distance larger than the width of a test strip, and a clamping position in which the clamping surfaces are engageable with opposing edges of a test strip, and an actuating element movably supported on the clamping jaw holder, the actuating element having at least one control surface arranged at an angle to a movement direction of the actuating element, the at least one control surface cooperating with a countersurface formed on at least one of the clamping jaws to move the damping jaw from the freeing position to the clamping position upon a movement of the actuating element.

2. A strip ejector according to claim 1, further characterized in that at least one movable clamping jaw is biased toward the freeing position.

3. A strip ejector according to claim 1, further characterized in that the damping jaws are formed on the longitudinal ends of a C-shaped bent clamping spring.

4. A strip ejector according to claim 3, further characterized in that the ends of the clamping spring which are turned toward one another have V-shaped notches for receiving the edges of the test strip.

5. A strip ejector according to claim 3, further characterized in that the actuating element has a recess on the side facing the clamping spring, wherein said recess widens in going toward an end of the actuating element, with surfaces of the side defining the recess forming the control surfaces.

6. A measuring device for the optical or amperemetrical measurement of test strips, having at least one test field to be wetted by a liquid, the device including a housing with a strip receiving compartment and an operating field, a test measuring arrangement, an evaluation and control device, and a current supply, the device characterized by a strip ejector comprising: a clamping jaw holder, at least two clamping jaws arranged on the clamping jaw holder, the clamping jaws being movable between a clamping position wherein the clamping jaws are engageable with a test strip inserted therebetween and a freeing position wherein the clamping laws are spaced apart a distance wider than a width of a test strip, an actuating element having at least one control surface arranged at an angle to the clamping jaw movement, the at least one control surface cooperating with a countersurface on at least one of the clamping jaws to move the clamping jaw from the freeing to the clamping position, the strip ejector being arranged in the measuring device, such that the damping jaws are disposed on opposing sides of the test strip receiving compartment, and the clamping jaw holder being arranged on the housing for slideable movement parallel to the insertion direction of a test strip between a rest position and an ejecting position.

7. A measuring device according to claim 6, further characterized in that the damping jaw bolder is biased towards the rest position.

8. A measuring device according to claim 6, further characterized in that the clamping jaw holder is movably fastened to a wall of said housing.

9. A measuring device according to claim 8, further characterized in that the clamping jaw holder is slid ably guided by a grove/rail guide on the housing wall.

10. A measuring device according to claim 8, further characterized in that the clamping jaw holder is snapped onto the housing wall.

11. A measuring device according to claim 8, further characterized in that the housing wall which carries the strip ejector is a battery cover for a battery compartment formed in the housing.

12. A measuring device according to claim 6, further characterized in that the actuating element is formed as a pusher which is slideably held on the damping jaw holder for slideable movement parallel to the movement direction of the clamping jaw holder.

13. A measuring device according to claim 6, further characterized in that the actuating element is formed by a push button which is supported on the clamping jaw holder for a movement perpendicular to the movement of the clamping jaw holder.

* * * * *

UNITED STATES PATENT AND TRADEMARK OFFICE
CERTIFICATE OF CORRECTION

PATENT NO. : 7,240,565 B2  Page 1 of 1
APPLICATION NO. : 11/122347
DATED : July 10, 2007
INVENTOR(S) : Eisenmann et al.

It is certified that error appears in the above-identified patent and that said Letters Patent is hereby corrected as shown below:

Claim 1, line 41, delete "damping" and insert --clamping--.

Claim 1, line 42, delete "damping" and insert --clamping--.

Claim 1, line 53, delete "damping" and insert --clamping--.

Claim 3, line 60, delete "damping" and insert --clamping--.

Claim 6, line 15, delete "laws" and insert --jaws--.

Claim 7, line 28, delete "damping" and insert --clamping--.

Claim 7, line 28, delete "bolder" and insert --holder--.

Claim 9, line 6, delete "slid ably" and insert --slideably--.

Claim 12, line 18, delete "damping" and insert --clamping--.

Signed and Sealed this

Twenty-third Day of October, 2007

JON W. DUDAS
*Director of the United States Patent and Trademark Office*